(12) United States Patent
Dunning et al.

(10) Patent No.: US 11,300,511 B2
(45) Date of Patent: Apr. 12, 2022

(54) PROBES FOR CHEMICAL ANALYSIS AND RELATED METHODS

(71) Applicant: Lantha, Inc., Austin, TX (US)

(72) Inventors: Samuel George Dunning, Washington, DC (US); Robert Toker, Spicewood, TX (US); Simon M. Humphrey, Lakeway, TX (US); Samuel T. Chill, Austin, TX (US); Dong Sub Kim, Austin, TX (US); Talitha Vanwie, Taylor, TX (US)

(73) Assignee: LANTHA, INC., Austin, TX (US)

(*) Notice: Subject to any disclaimer, the term of this patent is extended or adjusted under 35 U.S.C. 154(b) by 0 days.

(21) Appl. No.: 17/228,267

(22) Filed: Apr. 12, 2021

(65) Prior Publication Data

US 2021/0231564 A1    Jul. 29, 2021

Related U.S. Application Data

(63) Continuation of application No. PCT/US2020/064087, filed on Dec. 9, 2020.

(60) Provisional application No. 62/946,293, filed on Dec. 10, 2019.

(51) Int. Cl.
*G01N 21/64*   (2006.01)
*B01L 3/00*    (2006.01)

(52) U.S. Cl.
CPC .......... *G01N 21/643* (2013.01); *B01L 3/5023* (2013.01); *B01L 2300/021* (2013.01); *G01N 2021/6439* (2013.01)

(58) Field of Classification Search
None
See application file for complete search history.

(56) References Cited

U.S. PATENT DOCUMENTS

| | | | |
|---|---|---|---|
| 6,477,479 | B1 | 11/2002 | Mansky et al. |
| 7,416,703 | B2 | 8/2008 | Murray et al. |
| 7,968,346 | B2 | 6/2011 | Reed et al. |
| 8,105,552 | B2 | 1/2012 | Xiao et al. |

(Continued)

FOREIGN PATENT DOCUMENTS

| | | |
|---|---|---|
| CN | 102153575 A | 8/2011 |
| EP | 0259951 A2 | 3/1988 |

(Continued)

OTHER PUBLICATIONS

Dunning, et al., A Sensor for Trace H2O Detection in D2O, Apr. 13, 2017, 2017 Elsevier Inc., Chem 2, 579-589.

(Continued)

*Primary Examiner* — Lore R Jarrett
(74) *Attorney, Agent, or Firm* — William R. Childs; Childs Law

(57) ABSTRACT

The present disclosure relates to probes for analyzing a chemical composition, and related methods of analyzing a chemical composition and of manufacturing probes for analyzing a chemical composition. A benefit of the disclosed probes and methods can include luminescent chemical sensor arrays for rapid, accurate, portable and economical qualitative and quantitative analysis of a broad range of chemical compositions. A benefit of the methods disclosed herein can include the rapid, simple, and accurate analysis of trace chemicals present in chemical compositions.

12 Claims, 5 Drawing Sheets

(56) References Cited

U.S. PATENT DOCUMENTS

| | | | |
|---|---|---|---|
| 8,409,800 B2 | 4/2013 | Lu et al. | |
| 2007/0087452 A1 | 4/2007 | Parker et al. | |
| 2008/0207461 A1* | 8/2008 | Ermantraut | B01L 3/5085 506/8 |
| 2008/0219891 A1 | 9/2008 | McDevitt et al. | |
| 2010/0178208 A1* | 7/2010 | Xiao | B01L 3/50273 422/82.06 |
| 2012/0114089 A1 | 5/2012 | Potyrailo et al. | |
| 2012/0283575 A1 | 11/2012 | Rao et al. | |
| 2014/0145169 A1* | 5/2014 | Lee | C07D 263/57 257/40 |
| 2014/0287514 A1 | 9/2014 | Humphrey et al. | |

FOREIGN PATENT DOCUMENTS

| | | |
|---|---|---|
| WO | 2007100353 A2 | 9/2007 |
| WO | 2019067822 A1 | 4/2019 |

OTHER PUBLICATIONS

Extended European Search Report for European Patent Application 16 793 357.1 dated Jan. 2, 2019, pp. 1-8.

Hawes, et al., "Multichannel Luminescent Lanthanide Polymers as Ratiometric Sensors for D2O", Chem 2, Apr. 13, 2017, Elsevier Inc, 459-469.

Humphrey et al., Hysteretic sorption of light gases by a porous metal-organic frameworkcontaining tris(para-carboxylated) triphenylphosphine oxide, Chem. Commun. 2008, 2891-2893.

Humphrey et al., Metal-organophosphine and metal-organophosphonium frameworks withlayered honeycomb-like structures, Dalton Trans. 2009, 2298-2305.

Ibarra et al. "Gas sorption and luminescence properties of a terbium(III)-phosphine oxide coordination material withtwo-dimensional pore topology" Dalton Trans., 2012, 41, 8003 (Year: 2012).

Ibarra et al. "Molecular sensing and discrimination by a luminescent terbium-phosphine oxide coordination material" Chem.Commun., 2013, 49, 7156 (Year: 2013).

Ibarra et al. "Organic Vapor Sorption in a High Surface Area Dysprosium(III)-Phosphine Oxide Coordination Material" Inorg. Chem. 2012, 51, 12242-12247 (Year: 2012).

ISA/US, International Search Report/Written Opinion for PCT/US2020/064087, dated Mar. 3, 2021, 11 pages.

JPO, Notice of Rejection for application No. JP2017-556689 dated Apr. 14, 2020, 21 pages.

Kotek et al., Lanthanide(iii) Complexes of Novel Mixed Carboxylic-Phosphorous Acid Derivatives of Diethylenetriamine: A Step towards More Efficient MRI Contrast Agents. Chem. Eur. J 2003, 9, 5899-5915.

Luo et al. "A Facile Strategy for the Construction of Purely Organic Optical Sensors Capable of Distinguishing D2O from H2O", Angew. Chem. 2019, 131, 6346-6350.

Office Action for Chinese Application No. 201680027678.6, Issued by the National Intellectual Property Association ofthe People's Republic of China on Jun. 11, 2020, 10 pages.

Office Action for Chinese Application No. 201680027678.6, Issued by the National Intellectual Property Association ofthe People's Republic of China on Dec. 10, 2019, 9 pages.

Waggoner et al. "Magnetism of Linear [Ln3]9+ Oxo-Bridged Clusters (Ln = Pr, Nd) Supported inside a [R3PR']+ PhosphoniumCoordination Material" Inorg. Chem. 2014, 53, 12674-12676 (Year: 2014).

Wikipedia—Ultraviolet retrieved from internet Feb. 3, 2021 at https://en.wikipedia.org/wiki/ultraviolet, 30 pages.

Written Opinion of the International Searching Authority for International Application No. PCT/US2016/031593 datedOct. 17, 2016, pp. 1-6.

Zhan et al., "A Luminescent Mixed-Lanthanide-Organic Framework Sensor for Decoding Different Volatile OrganicMolecules," Analytical Chemistry, vol. 86, 2014, pp. 6648-6653.

\* cited by examiner

PROBES FOR CHEMICAL ANALYSIS AND RELATED METHODS

CROSS REFERENCE TO RELATED APPLICATIONS

The present application is a Continuation application, claiming priority to International Patent Application PCT/US20/64087, filed on Dec. 9, 2020, which claims priority from U.S. Provisional Patent Application No. 62/946,293, filed Dec. 10, 2019, the disclosures of which are herein incorporated by reference in their entirety.

TECHNICAL FIELD

The present disclosure relates to probes for analyzing a chemical composition, and related methods of analyzing a chemical composition and of manufacturing probes for analyzing a chemical composition. A benefit of the disclosed probes and methods can include luminescent chemical sensor arrays for rapid, accurate, portable and economical qualitative and quantitative analysis of a broad range of chemical compositions. A benefit of the methods disclosed herein can include the rapid, simple, and accurate analysis of trace chemicals present in chemical compositions.

BACKGROUND

Analysis of the identity and concentrations of various components in chemical compositions is of central importance to many industries. However, conventional methods of analyzing chemical compositions usually require taking samples on-site, transporting the samples to a remote testing facility, and using large, expensive equipment operated by highly trained, expensive personnel to provide test results from hours to months after those samples were taken. Also, there generally is no one universal test for chemical impurities in a composition. Instead, various separate tests usually need to be performed, depending on the analyte being tested for and the concentration of that analyte in the bulk material. There remains a need for real-time, on-site analysis of chemical compositions. There remains a need for a single, compact, inexpensive chemical analytical technique, and devices and probes therefore, that can test for a wide variety of impurities. There remains a need for an accurate chemical analysis technique that can be quickly and easily performed by a field worker having from 5 minutes to 2 hours of training.

SUMMARY

The present disclosure relates to probes for analyzing a chemical composition. In some embodiments, such a probe includes an array of luminescent chemical sensors mounted on a platform. In such embodiments, the array of luminescent chemical sensors includes at least one detection sensor, at least one control sensor, or a combination thereof, wherein the at least one detection sensor, if present, includes a combination of two or more detection lanthanide containing phosphorous compounds mounted onto a detection area of the platform; wherein the at least one control sensor, if present, includes at least one control lanthanide containing phosphorous compound mounted onto a control area of the platform; and wherein the platform is adhered to a base layer.

In some embodiments, the probe further includes at least one detection sensor mounted onto a detection area of a detection platform and at least one control sensor mounted onto a control area of a control platform, wherein the detection platform, the control platform, or a combination thereof, are adhered to the base layer.

In certain embodiments, the array of luminescent chemical sensors includes from 1 to 3 control sensors and from 1 to 50 detection sensors. In other embodiments, the array of luminescent chemical sensors includes 2 control sensors and from 1 to 50 detection sensors.

In certain embodiments, the control platform and the detection platform include a fibrous material, and the control platform and the detection platform are mounted on separate fibrous materials. In certain embodiments, the fibrous material includes a cellulosic material, a paper material, a silicone paper material, a borosilicate microfiber material, a glass microfiber material, a quartz microfiber material, a cotton fiber, or a combination thereof.

In certain embodiments, the at least one control lanthanide containing phosphorous compound is mounted directly onto the control platform without a binder; in some embodiments, the detection lanthanide containing phosphorous compounds are mounted directly onto the detection platform without a binder.

In certain embodiments, the base layer is formed of plastic, a paper, or wood, and the base layer has a length and a width equal to or greater than the array of luminescent chemical sensors. In some embodiments, the base layer forms a handle portion, which is located from about 1 mm to about 10 mm from the array of luminescent chemical sensors.

In certain embodiments, at least one of the control platform and the detection platform has a thickness of from about 0.1 mm to about 2 mm or less. In certain embodiments, at least one of the control platform and the detection platform has a longest measurement of from about 2 mm to about 60 mm. In some embodiments, at least one of the control area and the detection area have a square shape, a rectangular shape, a circular shape, an ovular shape, a triangular shape, a hexagonal shape, a polygonal shape, or a combination thereof.

In certain embodiments, the probe further includes an identification tag mounted on the base layer. In certain embodiments, the identification tag includes an optical tag or a radio frequency tag; or wherein the identification tag is mounted on a bottom of the probe or on a handle of the probe.

In certain embodiments, the at least one control lanthanide containing phosphorous compound includes at least one rare earth ion selected from the group consisting of La, Ce, Pr, Nd, Pm, Sm, Eu, Gd, Tb, Dy, Ho, Er, Tm, Yb, Lu, and Y. In certain embodiments, the combination of two or more detection lanthanide containing phosphorous compounds includes at least 2 different rare earth ions, wherein the rare earth ions are selected from the group consisting of La, Ce, Pr, Nd, Pm, Sm, Eu, Gd, Tb, Dy, Ho, Er, Tm, Yb, Lu, and Y.

In certain embodiments, the array of luminescent chemical sensors includes a lower wavelength control sensor and a higher wavelength control sensor. In such embodiments, the lower wavelength control sensor contains a lower wavelength ion X, wherein the higher wavelength control sensor contains a higher wavelength ion Z, wherein X and Z are different. In such embodiments, the array of luminescent chemical sensors includes at least one detection sensor containing a weight ratio of the lower wavelength ion X to the higher wavelength ion Z, wherein the weight ratio ranges from about 10:1 X:Z to about 1:10 X:Z.

In certain embodiments, the at least one detection sensor includes at least 2 lanthanide ions selected from the group consisting of Eu, Gd, and Tb; and wherein a weight ratio of the at least 2 lanthanide ions includes about 5:1 Tb:Eu, about 1:5 Tb:Eu, about 1:1:1 Eu:Gd:Tb, about 3:1:1 Eu:Gd:Tb, about 1:1:3 Eu:Gd:Tb, or about 1:3:1 Eu:Gd:Tb.

The present disclosure relates to methods of analyzing a chemical composition. Various embodiments of a method herein include providing a probe, wherein the probe includes an array of luminescent chemical sensors mounted on a platform, wherein the array of luminescent chemical sensors includes at least one detection sensor, at least one control sensor, or a combination thereof, wherein the at least one detection sensor, if present, includes a combination of two or more detection lanthanide containing phosphorous compounds mounted onto a detection area of the platform; wherein the at least one control sensor, if present, includes at least one control lanthanide containing phosphorous compound mounted onto a control area of the platform; and wherein the platform is adhered to a base layer; contacting the probe with the chemical composition for a test duration; exposing the probe to a test range of light; and measuring a color and an intensity of luminescence of the array of luminescent chemical sensors.

In some embodiments of methods herein, the array of luminescent chemical sensors includes at least one control sensor and at least one detection sensor, wherein the at least one control sensor includes at least one control lanthanide containing phosphorous compound mounted onto a control area of a control platform and the at least one detection sensor includes a combination of two or more detection lanthanide containing phosphorous compounds mounted onto a detection area of a detection platform, wherein the control platform and the detection platform are adhered to the base layer.

In certain embodiments, provided there is at least one chemical substance in the chemical composition, the method further includes identifying the at least one chemical substance in the chemical composition based on a measurement of the color and the intensity of luminescence of the array of luminescent chemical sensors. In certain embodiments, the method includes measuring a concentration of a chemical substance in the chemical composition based on a measurement of the color and the intensity of luminescence of the array of luminescent chemical sensors. In certain embodiments, the method further includes measuring the concentration of the at least one chemical substance in the chemical composition by comparing a ratio of wavelengths of luminescence emitted by a test sample to wavelengths of luminescence emitted by a concentration standard.

In certain embodiments, the method includes pre-scanning the array of luminescent chemical sensors prior to contacting the probe with the chemical composition for the test duration.

In certain embodiments, the chemical composition is in a liquid or a vapor phase. In certain embodiments, the at least one chemical substance includes deuterium, and the chemical composition includes water.

In certain embodiments, provided the probe further includes an identification tag mounted on the base layer, the method includes identifying the probe by scanning the identification tag.

The present disclosure relates to methods of manufacturing a probe for analyzing a chemical composition. Various embodiments of such methods herein include mounting an array of luminescent chemical sensors on an upper surface of a platform, wherein the array of luminescent chemical sensors includes at least one detection sensor, at least one control sensor, or a combination thereof; wherein the at least one detection sensor, if present, includes a combination of two or more detection lanthanide containing phosphorous compounds mounted onto a detection area of the platform; wherein the at least one control sensor, if present, includes at least one control lanthanide containing phosphorous compound mounted onto a control area of the platform; mounting at least two lining strips to the top and bottom of an upper surface of the platform; and adhering a lower surface of the platform to a base layer to form a probe.

In certain embodiments, mounting the array of luminescent chemical sensors on the upper surface of the platform includes spray coating the at least one detection sensor, the at least one control sensor, or a combination thereof, onto the platform. In certain embodiments, the method further includes heating the platform during or after spray coating. In certain embodiments, adhering the lower surface of the platform to the base layer includes ultrasonic welding.

In certain embodiments, the platform is formed from a binder free borosilicate microfiber material, a binder free glass microfiber material, a binder free quartz microfiber material, a cotton material, or a combination thereof. In certain embodiments, the base layer is formed from a plastic material. In certain embodiments, the at least two lining strips are formed from a plastic material.

In certain embodiments, the method further includes cutting the platform, base layer and at least two lining strips to form a plurality of probes.

Figure 1A:
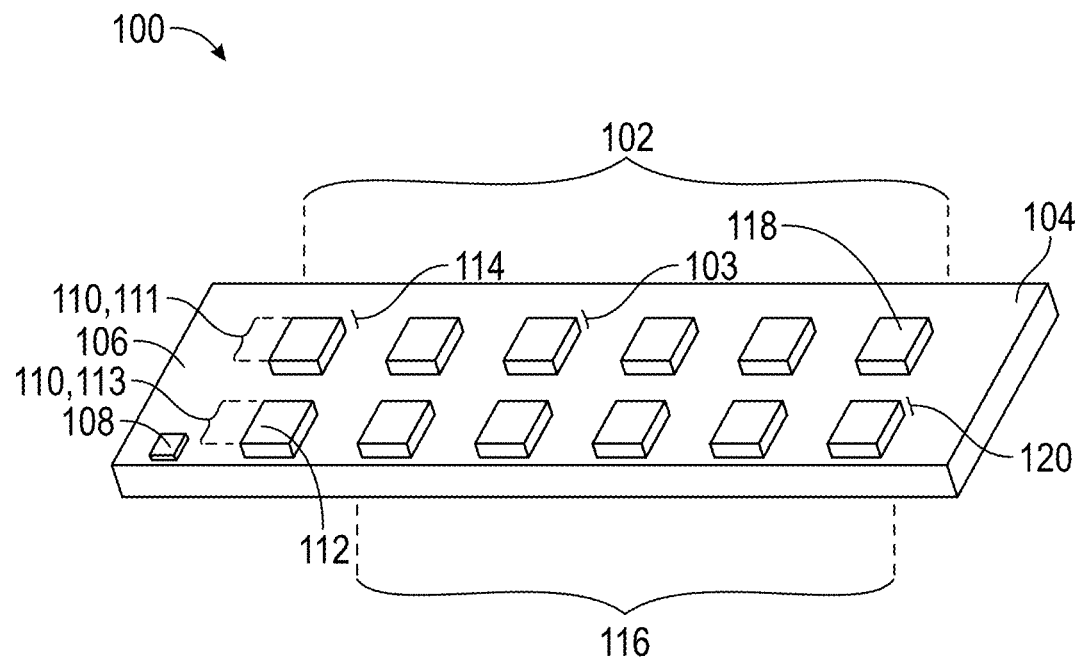
FIG. 1A shows a schematic illustration of a probe according to some embodiments herein.

The foregoing summary, as well as the following detailed description of the embodiments, will be better understood when read in conjunction with the attached drawings. For the purpose of illustration, there are shown in the drawings some embodiments, which may be preferable. It should be understood that the embodiments depicted are not limited to the precise details shown. Unless otherwise noted, the drawings are not to scale.

DETAILED DESCRIPTION

Unless otherwise noted, all measurements are in standard metric units.

Unless otherwise noted, all instances of the words "a," "an," or "the" can refer to one or more than one of the word or object that they modify.

Unless otherwise noted, the phrase "at least one of" means one or more than one of an object. For example, "at least one of the control platform and the detection platform" means one control platform, more than one control platform, one detection platform, more than one detection platform, or any combination thereof.

Unless otherwise noted, the term "about" refers to ±10% of the non-percentage number that is described, rounded to the nearest whole integer. For example, about 60 mm, would include 54 to 66 mm. Unless otherwise noted, the term "about" refers to ±5% of a percentage number. For example, about 20% would include 15 to 25%. When the term "about" is discussed in terms of a range, then the term refers to the appropriate amount less than the lower limit and more than the upper limit. For example, from about 1 mm to about 10 mm would include from 0.9 to 11 mm.

Unless otherwise noted, properties (height, width, length, ratio etc.) as described herein are understood to be averaged measurements.

Unless otherwise noted, the terms "provide", "provided" or "providing" refer to the supply, production, purchase, manufacture, assembly, formation, selection, configuration, conversion, introduction, addition, or incorporation of any element, amount, component, reagent, quantity, measurement, or analysis of any method or system of any embodiment herein.

Analysis of the identity and concentration of chemicals and components of chemical mixtures have broad applications across many industries and regulatory agencies. Just a few of these industries include environmental regulations, energy production, oil and gas, pharmaceuticals, chemical manufacturing, food production, hydrology, and geochemistry. Various chemical tests are important for detecting impurities and trace amounts of chemicals present in chemical mixtures. Among the myriad types of tests, some of these include performing quality assurance evaluations of chemical batch quality, testing deuterium oxide refinement, monitoring drug manufacturing processes, providing laboratory services to test land and water for contaminants, quality control testing of wholesale chemicals, monitoring environmental conditions, testing fuel integrity, analyzing chemical isotopes, and tracking moisture levels. Environmental monitoring is important for satisfying regulatory requirements and maintaining the safety of water supplies, including the monitoring of oil and gas wastewater from fracking operations, testing of reclaimed water, and testing of potable water quality. Fuel integrity is maintained by testing of high purity fuels for common contaminants, such as Diesel Exhaust Fluid (DEF) in aviation fuel. Dangerous chemicals in the environment can be identified, such as explosives and explosive taggants, and chemical warfare agent byproducts such as fluorine and cyanide.

Traditional methods of chemical analysis are generally time consuming and expensive. For the analysis of chemicals by traditional methods, samples often must be collected in sample containers and then packaged for transport, which can add days or weeks to the process. Large sample volumes may be required, adding to the difficulty of sample collection and transport. The samples must then be analyzed and a report generated, which may require the input of highly trained laboratory staff and the use of expensive laboratory equipment. Such analyses can include Fourier-transform infrared spectroscopy (FT-IR) or nuclear magnetic resonance measurements (NMR), the use of complex spectrophotometry (UV-Vis), or variations of mass spectroscopy (e.g. time of flight mass spectroscopy). High costs can also be involved for setting up the test facility and equipment. Overall, the process can take anywhere from several days up to several weeks to complete, and can cost hundreds to millions of dollars. And those costs only include the equipment. The time and costs of recruiting, training, and retaining highly skilled workers to interpret the test results can easily double or triple the cost. At the same time, new regulatory standards are causing companies to seek more chemical testing, which has been proving to be prohibitively expensive.

Embodiments disclosed herein can address the challenges presented by the current needs for chemical analyses, by allowing previously difficult tests to be made feasible. It has been discovered that certain phosphorous-based photoluminescent compounds exhibit changes in their relative luminescence emission intensity and wavelength when exposed to chemical solvents or impurities in chemical compositions. Among these, it has been discovered that tris(p-carboxylato) triphenylphosphine ($P(C_6H_4\text{-}p\text{-}CO_2H)_3$ or tctpH3) is an effective chromophore that allows for the efficient excitation of a number of lanthanide ions; a recently identified material named PCM-22 can be prepared in good yields with any $Ln^{3+}$ source from Pr—Yb (see US Patent Application 2018/0149599 and Dunning et al., Chem 2: 579-589, Apr. 13, 2017, the contents of which are hereby incorporated in their entirety).

It has been discovered that such compounds can used to make a probe for analyzing a chemical composition by serving as sensors for the identification and quantitative detection of a wide variety of solvents including liquids, gases, and solids. The present disclosure can provide a benefit of probes incorporating such sensors, to harness their broad sensitivity and specificity in a compact, portable, inexpensive, easy to use format that can quickly and easily identify and quantify a large number of components present in chemical mixtures, all in a single test. Such probes can provide enormous advantages in terms of time and money savings over traditional chemical analysis methods.

The embodiments of the present disclosure can provide a benefit of allowing a highly accurate testing of a broad variety of chemicals using minimal sample volumes. Such embodiments can provide a user friendly, rapid, simple and inexpensive way to identify trace chemicals present in chemical mixtures. Such embodiments can provide the benefits of quantitative accurate results down to concentrations of 10 ppm in as little as 1-2 minutes, with customizable options that can be tailored for specific applications, and costs of just a few dollars per test. Such embodiments can provide an advantage of simplicity such that the methods herein can be performed by field staff. With such advantages, there is no need for expensive and time-consuming sample collection, transport, and analysis by expensive personnel and lab equipment.

Figure 1B:
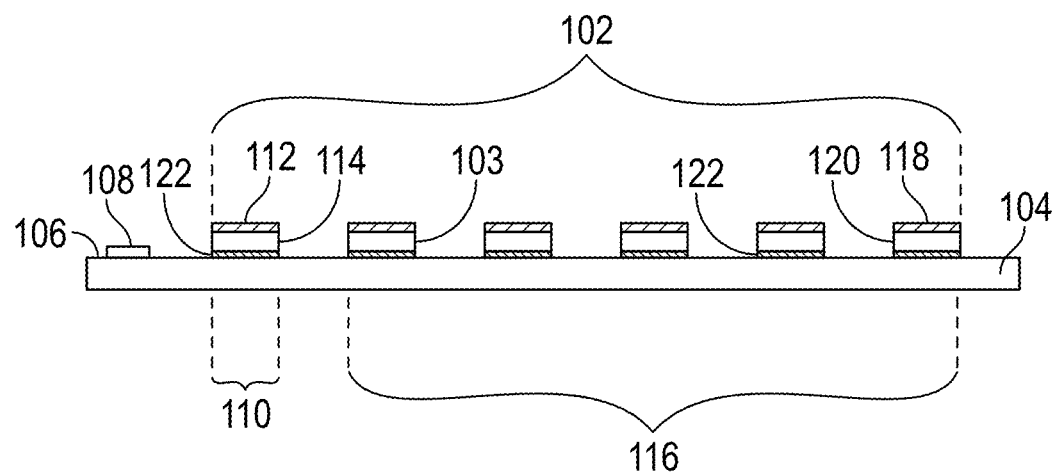
FIG. 1B shows a schematic side profile of the probe in FIG. 1A, according to some embodiments herein.

The present disclosure relates to probes for analyzing a chemical composition. As an illustration of a probe according to some embodiments disclosed herein, referring to FIG. 1A, probe 100 includes an array of luminescent chemical sensors 102 mounted on platform 103, wherein platform 103 is adhered to base layer 104, base layer 104 including handle portion 106 with identification tag 108 mounted on the base layer; control sensors 110 including lower wavelength control sensor 111 and higher wavelength control sensor 113, and including at least one control lanthanide containing phosphorus compound mounted onto a control area 112 on control platform 114; detection sensors 116 including two or more detection lanthanide containing phosphorus compounds mounted onto a detection area 118 on detection platform 120. Referring to the side profile in FIG. 1B, an array of luminescent chemical sensors 102 is mounted on platform 103, wherein platform 103 is adhered to base layer 104, base layer 104 including handle portion 106 with identification tag 108 mounted on the base layer, perhaps the handle portion; control sensor 110 including at least one control lanthanide containing phosphorous compound mounted onto a control area 112 of control platform 114; detection sensors 116 including two or more detection lanthanide containing phosphorous compounds mounted onto detection area 118 of detection platform 120; control platform 114 and detection platforms 120 being mounted to base layer 104 by binder 122.

Figure 2:
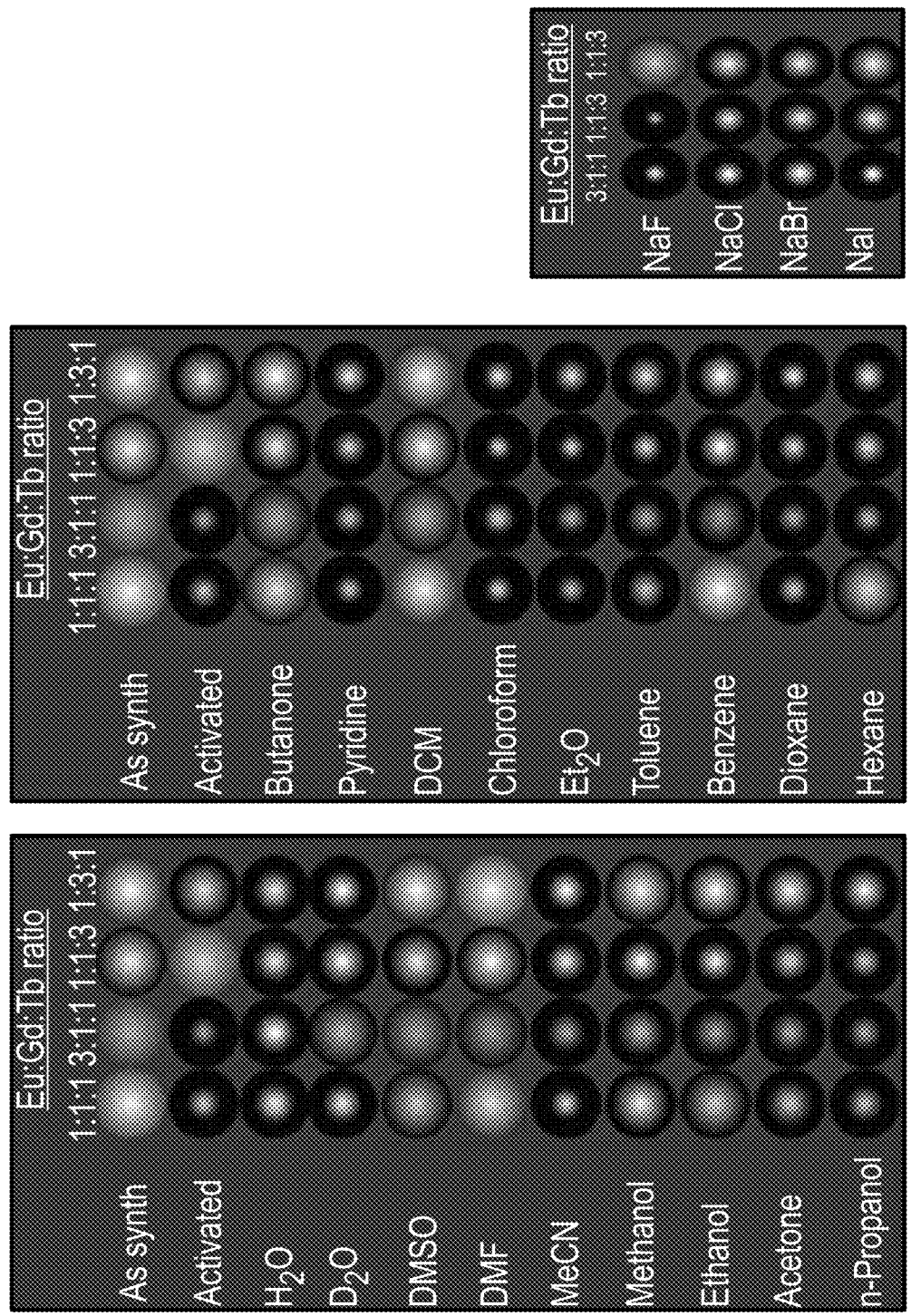
FIG. 2 is an image depicting eight-factor fingerprint signatures for a range of chemical solvents, according to some embodiments herein.

As a proof of concept for a probe according to embodiments disclosed herein, referring to FIG. 2, the image depicts eight-factor fingerprint signatures for a range of chemical solvents. Lanthanide ions Eu, Gd, and Tb are included in the detection sensors in the weight ratios shown. Circles show colors of the luminescence of the chemical sensors obtained upon exposure to each solvent. The size of each circle is representative of the intensity of luminescence emitted by the chemical sensors. Colors of the luminescence emitted range from light yellow to dark yellow, light orange to dark orange, light red to dark red, and light green to medium green.

Figure 3A:
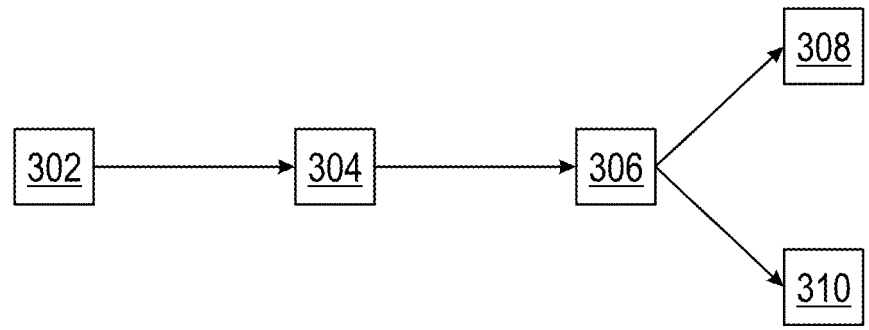
FIG. 3A is a flow chart depicting a method according to embodiments herein.
Figure 3B:
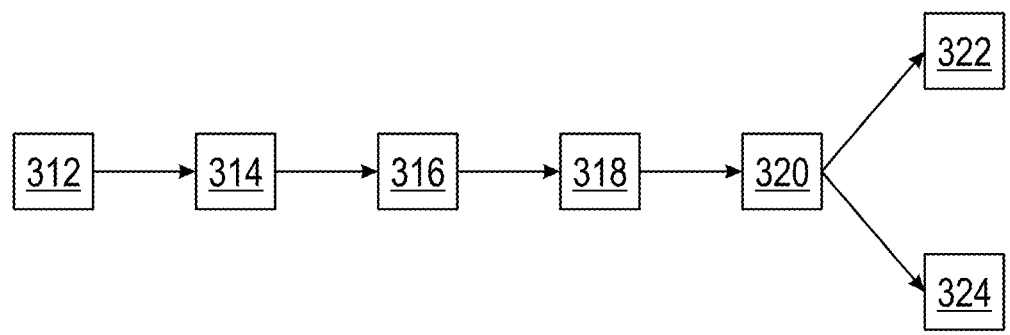
FIG. 3B is a flow chart depicting a method according to embodiments herein.

The present disclosure relates to methods of analyzing a chemical composition. As a general overview of a method according to embodiments herein, referring to FIG. 3A, the method includes providing a probe according to embodiments herein 302; contacting the probe with a chemical composition for a test duration 304; exposing the probe to a test range of light 306; and identifying at least one chemical substance in the chemical composition based on a measurement of the color and the intensity of luminescence of the array of luminescent chemical sensors 308; and/or measuring a concentration of a chemical substance in the chemical composition based on a measurement of the color and the intensity of luminescence of the array of luminescent chemical sensors 310. As a general overview of a method according to embodiments herein, referring to FIG. 3B, the method includes providing a probe according to embodiments herein 312; exposing the probe to a baseline range of light 314; measuring the color and the intensity of luminescence of the array of luminescent chemical sensors, thereby pre-scanning the array of luminescent chemical sensors prior to contacting the probe with a chemical composition 316; exposing the pre-scanned probe to a test range of light 318; contacting the probe with a chemical composition for a test duration 320; and identifying at least one chemical substance in the chemical composition based on a measurement of the color and the intensity of luminescence of the array of luminescent chemical sensors 322; and/or measuring a concentration of a chemical substance in the chemical composition based on a measurement of the color and the intensity of luminescence of the array of luminescent chemical sensors 324.

Figure 4:
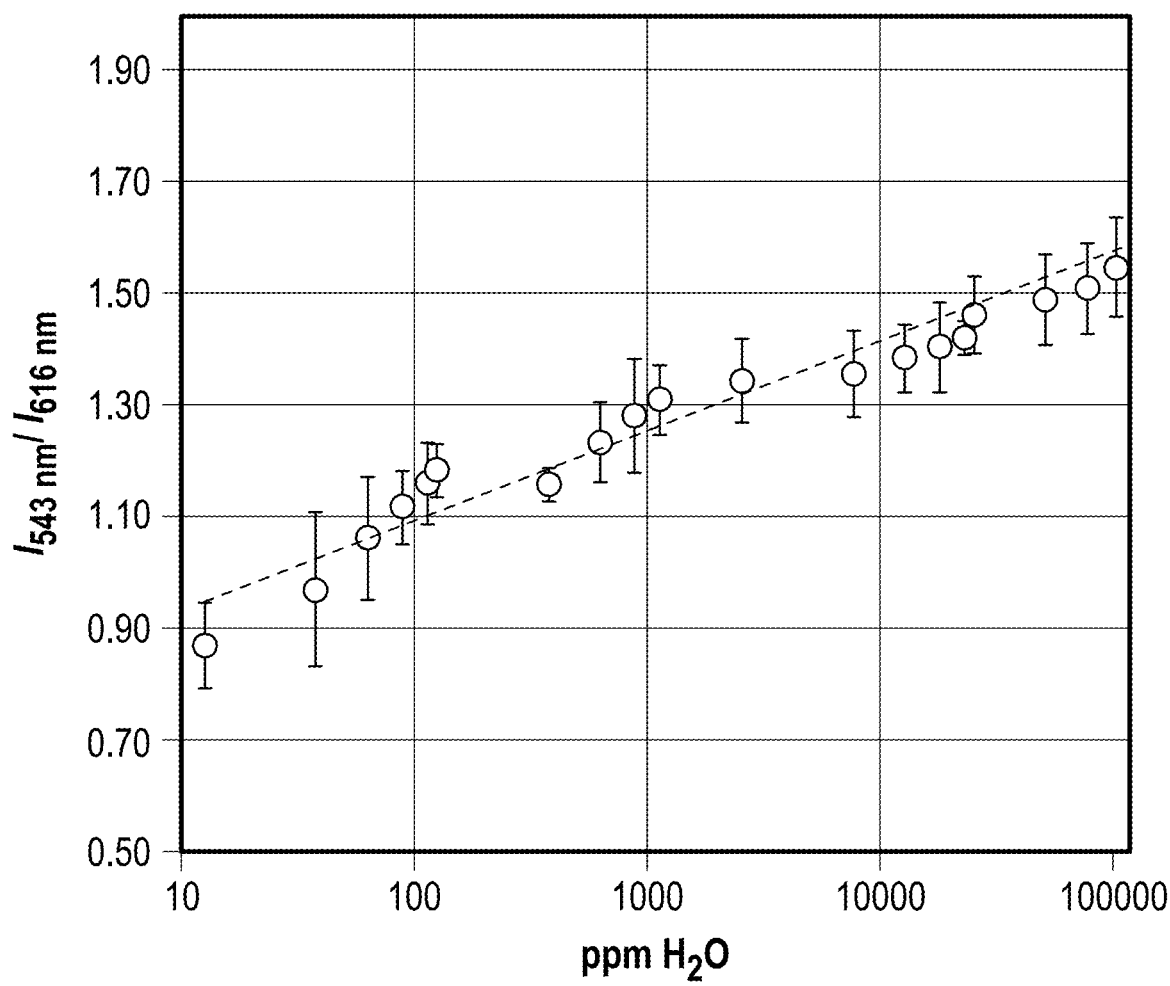
FIG. 4 is a graph of photoemission response ratios for addition of trace H2O to Eu1:Tb5-PCM-22 pre-soaked in D2O.

As an illustration of a method according to embodiments herein, referring to FIG. 4, the graph includes photoemission response ratios for addition of trace H2O to Eu1:Tb5-PCM-22 pre-soaked in D2O.

The present disclosure relates to methods of manufacturing a probe for analyzing a chemical composition. As a general overview of a method according to embodiments herein, the method includes mounting an array of luminescent chemical sensors on an upper surface of a platform, wherein the array of luminescent chemical sensors includes at least one detection sensor, at least one control sensor, or a combination thereof; wherein the at least one detection sensor, if present, includes a combination of two or more detection lanthanide containing phosphorous compounds mounted onto a detection area of the platform; wherein the at least one control sensor, if present, includes at least one control lanthanide containing phosphorous compound mounted onto a control area of the platform; mounting at least two lining strips to the top and bottom of an upper surface of the platform; and adhering a lower surface of the platform to a base layer to form a probe.

Figure 5:
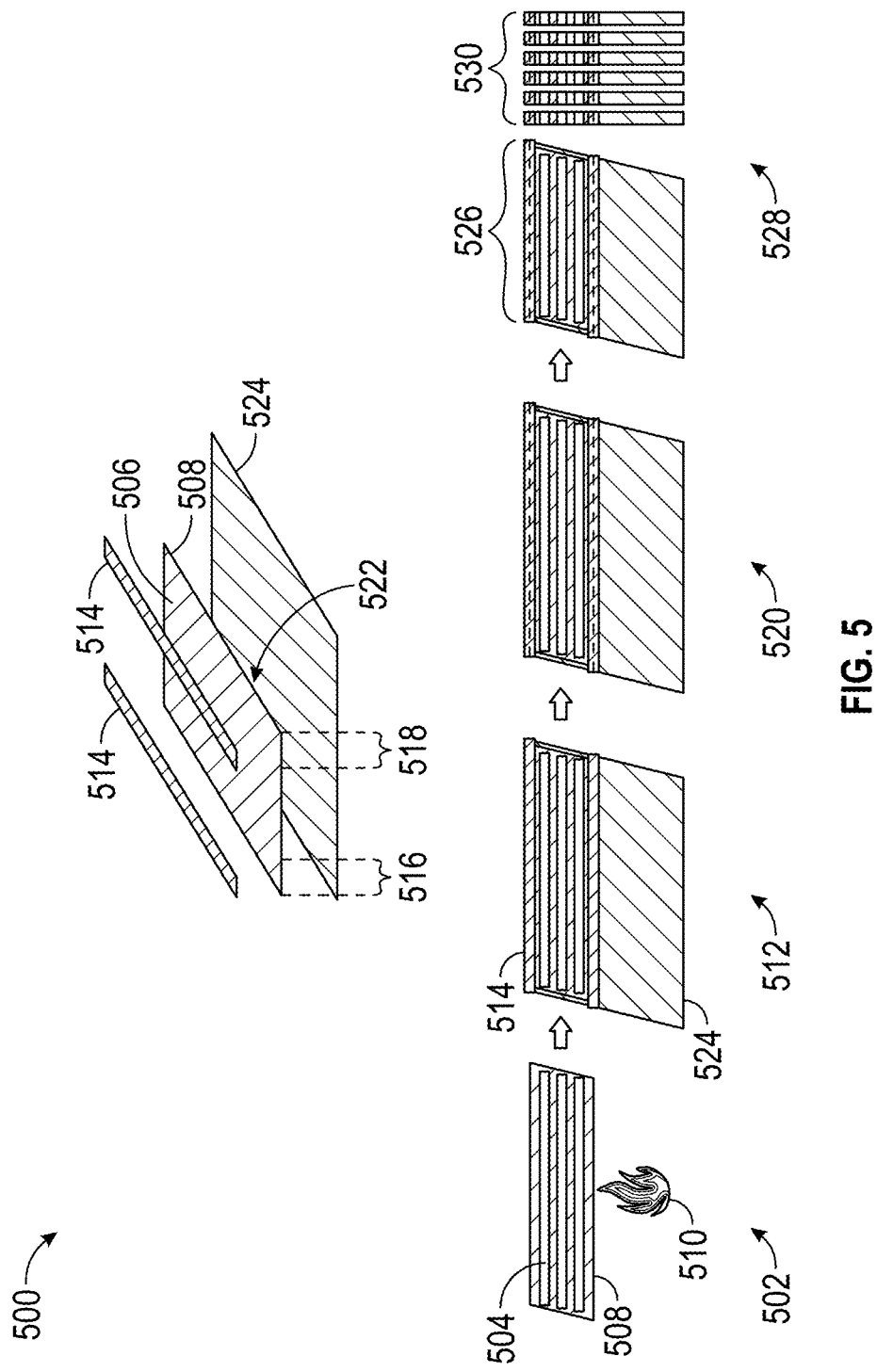
FIG. 5 is a schematic illustration of a method according to embodiments herein, and a probe according to embodiments herein.

As an illustration of a method of manufacturing a probe according to embodiments herein, referring to FIG. 5, method 500 includes spray coating 502 at least one detection sensor, at least one control sensor, or a combination thereof 504 onto an upper surface 506 of platform 508; heating 510 platform 508 during or after spray coating; mounting 512 at least two lining strips 514 to a top 516 and bottom 518 of upper surface 506 of platform 508; adhering 520 a lower surface 522 of platform 508 to base layer 524 to form probe 526; and cutting 528 platform 508, base layer 524 and at least two lining strips 514 to form plurality of probes 530.

As an illustration of a method of manufacturing a probe according to embodiments herein, referring to FIG. 6, method 600 includes spray coating 602 at least one detection sensor, at least one control sensor, or a combination thereof 604 onto an upper surface 606 of platform 608; heating 610 platform 608 during or after spray coating; mounting 612 at least two lining strips 614 to a top 616 and bottom 618 of upper surface 606 of platform 608; adhering 620 a lower surface 622 of platform 608 to base layer 624 to form probe 626; and cutting 628 platform 608, base layer 624 and at least two lining strips 614 to form plurality of probes 630.

Chemical Analysis Probes of Various Embodiments

The present disclosure relates to probes for analyzing a chemical composition. In various embodiments, such a probe includes an array of luminescent chemical sensors mounted on a platform. In some embodiments, the array of luminescent chemical sensors includes at least one control sensor and at least one detection sensor. In some embodiments, the array of luminescent chemical sensors includes at least one detection sensor or at least one control sensor.

In various embodiments, the at least one detection sensor, if present, includes a combination of two or more detection lanthanide containing phosphorous compounds. In various embodiments, the at least one control sensor, if present, includes at least one control lanthanide containing phosphorous compound.

In certain embodiments, the at least one detection sensor, the at least one control sensor, or a combination thereof, are mounted on a platform. In some embodiments, the platform can be formed of a single piece of material, on which the array of luminescent chemical sensors is mounted. In such embodiments, the at least one detection sensor, if present, is mounted onto a detection area of the platform; and the at least one control sensor, if present, is mounted onto a control area of the platform. In such embodiments, the platform is adhered to a base layer.

In certain embodiments, the at least one control sensor includes at least one control lanthanide containing phosphorous compound mounted onto a control area of a control platform, and the at least one detection sensor includes a combination of two or more detection lanthanide containing phosphorous compounds mounted onto a detection area of a detection platform. In such embodiments, the control platform and the detection platform can be formed of one or more separate pieces of platform material. In such embodiments, the control platform and the detection platform are adhered to the base layer.

In an embodiment, a benefit of a control sensor can be to anchor/calibrate the device to remove any systematic error. For example, if one camera processes images with a consistent red shift, then the control spots will generate a calibration curve where all spots are equally red-shifted and should therefore not read any differently to other devices.

In an embodiment, a benefit to multiple detection sensors can be to provide increased accuracy/precision for trace detection studies and to serve as an initial platform for array sensing. If too few detecting sensors are used, then there could be a decrease in accuracy/precision or result in not being able to identify certain chemicals.

In certain embodiments, the array of luminescent chemical sensors includes from 1 to 3 control sensors and from 1 to 6 detection sensors, including from 1 to 50 sensors, including 1 to 100 sensors, including 1 to 1000 sensors. In other embodiments, the array of luminescent chemical sensors includes 2 control sensors and from 1 to 6 detection sensors.

In certain embodiments, the platform, or the control platform and the detection platform, include a fibrous material. In certain embodiments, the platform is formed of a single fibrous material. In certain embodiments, the control platform and the detection platform are mounted on separate fibrous materials.

It has been discovered that the lanthanide containing phosphorous compounds for a wide variety of chemical compounds are so reactive and sensitive that adhering them directly to a support layer, such as the base layer, using an adhesive or binder, can adversely affect the ability of these materials to sense analytes. It has been discovered that this adverse contamination can be avoided by depositing lanthanide containing phosphorous compounds onto fibrous materials, wherein the lanthanide containing phosphorous compounds are excluded from direct contact with a binder or adhesive. In certain embodiments, the fibrous material includes a cellulosic material, a paper material, a silicone paper material, or a combination thereof. Considering the high sensitivity and reactivity of the lanthanide containing phosphorous compounds for a wide variety of chemical compounds, the present disclosure of a control platform and a detection platform mounted on separate fibrous materials can provide a benefit of preventing cross-contamination between the control sensors and the detection sensors during production, storage, and/or testing. Such a benefit can present a great advantage for a compact configuration for the analysis of multiple components in complex chemical mixtures in a single test.

To reduce costs, experimentation is underway to discover a method of adhering the lanthanide containing phosphorous material directly to the base layer using an adhesive. In certain embodiments, the control area and detection area include the lanthanide containing phosphorous material adhered directly to an adhesive layer.

In more detail, in some embodiments, at least one control lanthanide containing phosphorous compound is mounted directly onto the control platform without a binder; in some embodiments, the detection lanthanide containing phosphorous compounds are mounted directly onto the detection platform without a binder. The lanthanide containing phosphorous compounds disclosed herein possess a strong reactivity toward a wide variety of chemical compounds, presenting challenges for the analysis of a large number of different chemicals in a compact, portable probe format. Many embodiments of the present disclosure address this challenge by providing chemical sensors including lanthanide containing phosphorous compounds mounted directly onto a control platform or a detection platform without the use of a binder, preventing or reducing reaction of the binder material with the lanthanide containing phosphorous compounds. In some embodiments, a binder can be used to adhere a bottom surface of the control platform or the detection platform to the base layer, while the chemical sensors are mounted on a top surface of the control platform or the detection platform. In such embodiments, contact of the chemical sensors with the binder is avoided or reduced, thus providing an advantage of preventing or reducing the chances of reaction of the lanthanide containing phosphorous compounds with the binder, while allowing a compact, portable, inexpensive, disposable test format for analysis of multiple chemicals. In embodiments wherein the control platform or the detection platform includes a fibrous material, such embodiments can also provide a benefit of allowing the mounting of the chemical sensors in separate or discrete areas or shapes, further aiding the prevention of cross contamination between different chemical sensors.

In other embodiments, an adhesive layer is mounted onto the base layer, and the array of luminescent chemical sensors is mounted directly onto the adhesive layer, provided that the lanthanide containing phosphorous compounds do not react in any way with the binder. In certain embodiments, such an adhesive layer can be sprayed onto the base layer. In certain embodiments, the array of luminescent chemical sensors is selectively printed onto the adhesive layer. In certain embodiments, either of the control lanthanide containing phosphorous compounds and the detection lanthanide phosphorous containing compounds can be mounted onto an adhesive layer that is in turn mounted onto the control platform or the detection platform, respectively. In certain embodiments, at least one control lanthanide containing phosphorous compound, the detection lanthanide containing phosphorous compounds, or combinations thereof, can be sprayed by ink-jet, screen printing, or other methods of variable printing directly onto an adhesive layer, or directly onto the base layer, or directly onto a platform.

In certain embodiments, the base layer is formed of a plastic, a paper, or wood, and the base layer has a length and a width equal to or greater than the array of luminescent chemical sensors. In some embodiments, the base layer forms a handle portion, which is located from about 1 mm to about 10 mm from the array of luminescent chemical sensors. In certain embodiments, the handle portion is located from about 3 mm to about 7 mm from the array of luminescent chemical sensors. Considering the broad reactivity of the lanthanide containing phosphorous compounds for different chemicals, any contact or contamination with a user's fingers, gloves, or other user-introduced contamination can interfere with the correct functioning of the chemical sensors. A handle portion as disclosed herein can provide a benefit of allowing the handling of a probe without the need to touch the remainder of the base layer, or the array of chemical sensors, thus preventing contamination of the chemical sensors and preventing potential false readings.

In certain embodiments, at least one of the platform, the control platform and the detection platform has a thickness of from about 0.1 mm to about 2 mm or less. In certain embodiments, at least one of the control platform and the detection platform has a thickness of from about 0.5 mm to about 1.5 mm. In certain embodiments, at least one of the control platform and the detection platform has a thickness of from about 0.7 mm to about 1.0 mm. In certain embodiments, at least one of the control platform and the detection platform has a thickness of about 1 mm or less. In certain embodiments, at least one of the control platform and the detection platform has a longest measurement of from about 2 mm to about 60 mm. In certain embodiments, at least one of the control platform and the detection platform has a longest measurement of from about 10 mm to about 60 mm. In certain embodiments, at least one of the control platform and the detection platform has a longest measurement of from about 30 mm to about 40 mm. In some embodiments, at least one of the control area and the detection area have a square shape, a rectangular shape, a circular shape, an ovular shape, a triangular shape, a hexagonal shape, a polygonal shape, or a combination thereof. In certain embodiments, at least one control lanthanide containing phosphorous compound and the two or more detection lanthanide containing phosphorous compounds can be mounted onto the control area and the detection area, respectively, by being sprayed onto, ink-jetted onto, condensed onto, or embedded in the control area or the detection area. In certain embodiments, a fibrous material according to embodiments of the control platform or the detection platform can be contacted with one or more solutions containing at least one control lanthanide containing phosphorous compound or the two or more detection lanthanide containing phosphorous compounds, allowed to dry, and cut, stamped, or marked in order to form the control platform or the detection platform.

In certain embodiments, the probe includes an identification tag mounted on the base layer. In certain embodiments, the identification tag includes an optical tag or a radio frequency tag. In certain embodiments, the identification tag is mounted on a bottom of the probe or on a handle of the probe. The performing of chemical tests presents challenges of keeping track of exactly what tests have been conducted with each probe; for example, has a particular probe been pre-scanned for sensor viability, has a control test been run, or has a detection test already been run, so that a second test should not be conducted? Such embodiments of probes including an identification tag can provide a solution to such challenges by allowing the tracking of a particular probe using a unique identification tag for each probe, to track which test steps have been conducted with each probe, and to match any pre-scanning or baseline test runs with subsequent detection measurements. Such embodiments can also provide an advantage of preventing the re-use of a probe after a detection test has been run.

Lanthanide Containing Phosphorous Compounds of Various Embodiments

Embodiments of probes and methods herein include various luminescent compounds including a phosphorous atom with one or more carboxyl groups that are coordinated with one or more metallic ions. Such metallic ions can include one more lanthanide ions, yttrium ions, and combinations thereof.

In certain embodiments, the luminescent compounds can include one or more light absorbing groups. In certain embodiments, the light absorbing groups are coupled to the carboxyl groups. In some embodiments, the light absorbing groups can include one or more conjugated groups, aromatic groups, phenyl groups, aryl groups, alkenyl groups, alkynyl groups, azido groups, and cyano groups.

The luminescent compounds of various embodiments can include various types of metallic ions. In some embodiments, the luminescent compounds can include a single metallic ion. In some embodiments, the luminescent compounds can include a plurality of the same metallic ions, or a plurality of different metallic ions. In certain embodiments, the luminescent compounds include a plurality of metallic ions at different weight ratios. In certain embodiments, such weight ratios can include 1:1, 2:1, 1:3, 3:1, 1:1:1, 2:1:1, 1:2:1, 1:1:2, 5:1, 1:5, 3:1:1, 1:1:3, 1:3:1, and combinations thereof. The luminescent compounds herein can possess a reactivity to a wide variety of chemical compounds, where the color and intensity of the light emitted in reaction with various chemical compounds can vary widely based not only on the particular compound but on the amount of the compound present in a chemical composition. The luminescent compounds herein can vary substantially in the color and intensity of emitted light in response to the identity and concentrations of various chemical compounds, depending on the particular metallic ions included in the luminescent compounds, the number of different metallic ions included, and also the particular weight ratios of the different metallic ions included in the luminescent compounds. It has been discovered that the identity, number, and weight ratios of different metallic ions included in the luminescent compounds can thus be varied on a probe in order to provide a benefit of greatly increased specificity and sensitivity for the detection of a wide variety of chemical compounds in a chemical composition.

In certain embodiments, the at least one control lanthanide containing phosphorous compound includes at least one rare earth ion selected from the group consisting of La, Ce, Pr, Nd, Pm, Sm, Eu, Gd, Tb, Dy, Ho, Er, Tm, Yb, Lu, and Y. In some embodiments, the at least one control lanthanide containing phosphorous compound contains one rare earth ion. A benefit of a control sensor containing one phosphorous compound that one rare earth ion can be that it facilitates calibration by providing a control reference point. In some embodiments, the at least one control lanthanide containing phosphorous compound contains terbium ($Tb^{3+}$) and gadolinium ($Gd^{3+}$) in the same framework, e.g., TbPCM-22. A benefit of a control sensor containing one phosphorous compound network containing terbium ($Tb^{3+}$) and gadolinium ($Gd^{3+}$) can be that it balances or faciliates the balancing of signal intensity (brightness) between a sensor and a control. Without wishing to be bound by theory, it is believed that $Gd^{3+}$ serves as a place holder for the framework formation and not an active component in terms of luminescence property, such that having $Gd^{3+}$ effectively dilutes the 'concentration' of $Tb^{3+}$ in the framework.

In certain embodiments, the combination of two or more detection lanthanide containing phosphorous compounds includes at least 2 different rare earth ions, wherein the rare earth ions are selected from the group consisting of La, Ce, Pr, Nd, Pm, Sm, Eu, Gd, Tb, Dy, Ho, Er, Tm, Yb, Lu, and Y. In some embodiments, the combination of two or more detection lanthanide containing phosphorous compounds includes Tb, Eu, and Tm. In some embodiments, the combination of two or more detection lanthanide containing phosphorous compounds includes Eu, Gd, and Tb.

The phosphorous atoms of the luminescent compounds can be in various forms. In certain embodiments, the phosphorous atoms can be in non-oxidized form. In certain embodiments, the phosphorous atoms can be oxidized. In certain embodiments, the phosphorous atoms can be oxidized by post-synthetic oxidation methods.

In certain embodiments, the luminescent compounds can have various structures. In certain embodiments, the luminescent compounds are porous, or in the form of a crystalline lattice. In certain embodiments, the metallic ions in the luminescent compounds coordinate with carboxyl groups on adjacent luminescent compounds to form a crystalline lattice. In some embodiments, the luminescent compounds have a honeycomb-like structure, are in the form of two-dimensional honeycomb sheets, stacked in an eclipsed arrangement to result in a three-dimensional solid having large hexagonal channels, or a combination thereof.

In certain embodiments, the luminescent compounds have various surface areas. In certain embodiments, the luminescent compounds have surface areas of from about 50 m2/g to about 1000 m2/g. In certain embodiments, the luminescent compounds have surface areas of from about 250 m2/g to about 800 m2/g. In certain embodiments, the luminescent compounds have surface areas of from about 500 m2/g to about 750 m2/g. In certain embodiments, the luminescent compounds have surface areas of from about 500 m2/g to about 600 m2/g.

The luminescent compounds can have various quantum yields. In some embodiments, the luminescent compounds have absolute quantum yields of photoluminescence WO that range from about 20% to about 95%. In certain embodiments, the luminescent compounds have ΦPL values that range from about 35% to about 95%. In certain embodiments, the luminescent compounds have ΦPL values that range from about 50% to about 90%. In certain embodiments, the luminescent compounds have ΦPL values that range from about 80% to about 90%.

In some embodiments, the luminescent compounds of the present disclosure include one or more of compounds 1-9, as presented herein.

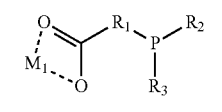
(1)

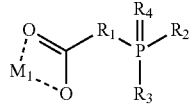
(2)

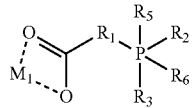
(3)

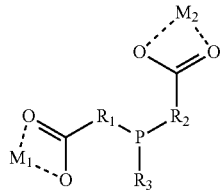
(4)

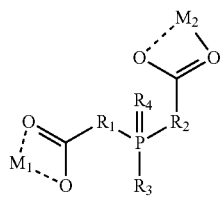
(5)

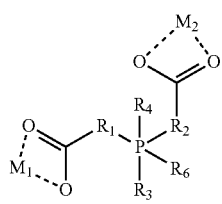
(6)

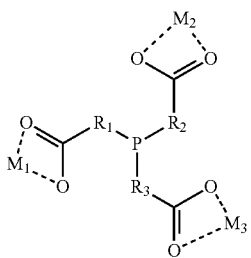
(7)

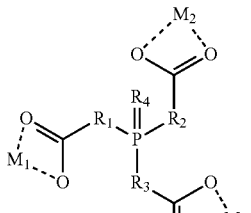
(8)

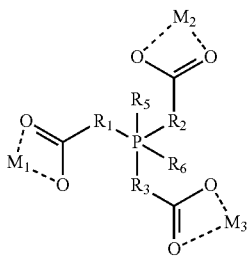
(9)

In some embodiments, each of M1, M2 and M3 in compounds 1-9 represent metallic ions that include, without limitation, La, Ce, Pr, Nd, Pm, Sm, Eu, Gd, Tb, Dy, Ho, Er, Tm, Yb, Lu, Y, and combinations thereof. In some embodiments, each of M1, M2 and M3 in compounds 1-9 represent lanthanide ions that include, without limitation, Tb, Eu, Tm, and combinations thereof.

In some embodiments, each of R1, R2, R3, R5 and R6 in compounds 1-9 include, without limitation, light absorbing groups (as described previously), hydrogen (where feasible), oxygen, carbon-containing groups, aliphatic groups, non-aromatic groups, conjugated groups, aromatic groups, phenyl groups, aryl groups, heterocyclic groups, cyclic groups, alkyl groups, alkenyl groups, alkynyl groups, halides, azido groups, cyano groups, methyl groups, nitrogen containing groups, alkoxyl groups, carboxyl groups, carbonyl groups, ethers, esters, acetyl groups, acetoxy groups, acetomethoxy groups, acetoxymethyl esters, acetoxyalkyl esters, alkoxyalkyl esters, boron containing groups, silicon containing groups, phosphorous containing groups, sulfur containing groups, arsenic containing groups, germanium containing groups, selenium containing groups, aluminum containing groups, tin containing groups, antimony containing groups, tellurium containing groups, lead containing groups, bismuth containing groups, polonium containing groups, cycloamines, heteroatoms, and combinations thereof.

In some embodiments, each of R1, R2 and R3 in compounds 1-9 include light absorbing groups. In some embodiments, the light absorbing groups include a phenyl group.

In some embodiments, R4 in compounds 2, 5 and 8 include, without limitation, O, S, NR7, CR8R9, Se, and combinations thereof. In some embodiments, each of R7, R8, and R9 includes, without limitation, light absorbing groups, hydrogen, oxygen, carbon-containing groups, aliphatic groups, non-aromatic groups, conjugated groups, aromatic groups, phenyl groups, aryl groups, heterocyclic groups, cyclic groups, alkyl groups, alkenyl groups, alkynyl groups, halides, azido groups, cyano groups, methyl groups, nitrogen containing groups, alkoxy groups, carboxyl groups, carbonyl groups, ethers, esters, acetyl groups, acetoxy groups, acetomethoxy groups, acetoxymethyl esters, acetoxyalkyl esters, alkoxyalkyl esters, boron containing groups, silicon containing groups, phosphorous containing groups, sulfur containing groups, arsenic containing groups, germanium containing groups, selenium containing groups, aluminum containing groups, tin containing groups, antimony containing groups, tellurium containing groups, lead containing groups, bismuth containing groups, polonium containing groups, cycloamines, heteroatoms, and combinations thereof. In some embodiments, R4 includes oxygen, sulfur, or selenium.

The R4 group can be appended to the luminescent compounds of the present disclosure in various manners. For instance, in some embodiments, the R4 group is appended to the luminescent compound through post-synthetic modification steps.

In some embodiments, the luminescent compounds of the present disclosure include compound 8. In some embodiments, each of R1, R2, and R3 in compound 8 includes phenyl groups. In some embodiments, each of M1, M2, and M3 in compound 8 includes Tb(III). In some embodiments, R4 includes oxygen that has been appended through post-synthetic oxidation.

In some embodiments, the luminescent compounds of the present disclosure include compound 9. In some embodiments, each of R1, R2, and R3 in compound 9 includes phenyl groups. In some embodiments, each of M1, M2, and M3 in compound 9 includes Tb(III). In some embodiments, each of R5 and R6 in compound 9 includes, without limitation, carbon-containing groups (e.g., aliphatic or aromatic carbons), hydrogen, and combinations thereof.

In certain embodiments, the array of luminescent chemical sensors includes a lower wavelength control sensor and a higher wavelength control sensor. In such embodiments, the lower wavelength control sensor contains a lower wavelength ion X, and the higher wavelength control sensor contains a higher wavelength ion Z, wherein X and Z are different. In such embodiments, the array of luminescent chemical sensors includes at least one detection sensor containing a weight ratio of the lower wavelength ion X to the higher wavelength ion Z, wherein the weight ratio ranges from about 10:1 X:Z to about 1:10 X:Z. In certain embodiments, the weight ratio ranges from about 8:1 X:Z to about 1:8 X:Z. In certain embodiments, the weight ratio ranges from about 5:1 X:Z to about 1:5 X:Z.

In certain embodiments, the at least one detection sensor includes at least 2 lanthanide ions selected from the group consisting of Eu, Gd, and Tb; and wherein a weight ratio of the at least 2 lanthanide ions includes about 5:1 Tb:Eu, about 1:5 Tb:Eu, about 1:1:1 Eu:Gd:Tb, about 3:1:1 Eu:Gd:Tb, about 1:1:3 Eu:Gd:Tb, or about 1:3:1 Eu:Gd:Tb. In certain embodiments, a weight ratio of the at least 2 lanthanide ions includes about 4:1 Tb:Eu, about 3:1 Tb:Eu, about 2:1 Tb:Eu, about 1:1 Tb:Eu, about 1:4 Tb:Eu, about 1:3 Tb:Eu, about 1:2 Tb:Eu, about 2:1:1 Eu:Gd:Tb, about 1:2:1 Eu:Gd:Tb, about 1:1:2 Eu:Gd:Tb, or combinations thereof. In certain embodiments, the at least one detection sensor includes at least 2 lanthanide ions selected from the group consisting of Eu, Gd, and Tb in a weight ratio ranging from about 10:1:1 to about 1:10:1 to about 1:1:10, respectively.

Chemical Composition Analysis Methods of Various Embodiments

The present disclosure relates to methods of analyzing a chemical composition. Various embodiments of methods herein include providing a probe, wherein the probe includes an array of luminescent chemical sensors mounted on a platform. In certain embodiments, the array of luminescent chemical sensors includes at least one control sensor and at least one detection sensor. In some embodiments, the array of luminescent chemical sensors includes at least one detection sensor or at least one control sensor. Such embodiments can provide for flexibility in the types of probes that can be used during analysis of a chemical composition.

In certain embodiments, the at least one detection sensor, the at least one control sensor, or a combination thereof, are mounted on a platform. In some embodiments, the platform can be formed of a single piece of material, on which the array of luminescent chemical sensors is mounted. In such embodiments, the at least one detection sensor, if present, is mounted onto a detection area of the platform; and the at least one control sensor, if present, is mounted onto a control area of the platform. In such embodiments, the platform is adhered to a base layer. In various embodiments, the method includes contacting the probe with the chemical composition for a test duration; exposing the probe to a test range of light; and measuring a color and an intensity of luminescence of the array of luminescent chemical sensors.

In certain embodiments the array of luminescent chemical sensors includes at least one control sensor and at least one detection sensor, wherein the at least one control sensor includes at least one control lanthanide containing phosphorous compound mounted onto a control area of a control platform and the at least one detection sensor includes a combination of two or more detection lanthanide containing phosphorous compounds mounted onto a detection area of a detection platform, wherein the control platform and the detection platform are adhered to the base layer. In some embodiments, the control platform and the detection platform can be formed from one or more separate pieces of platform material. In various embodiments, the method includes contacting the probe with the chemical composition for a test duration; exposing the probe to a test range of light; and measuring a color and an intensity of luminescence of the array of luminescent chemical sensors.

The probes can be contacted with various chemical compositions. In certain embodiments, the chemical composition is in a liquid phase or a vapor phase, or combinations thereof. In certain embodiments, the chemical composition includes a solid. In certain embodiments including a liquid chemical composition, the liquid can include solutions, solvent feedstocks, environmental water solutions, reservoirs, waste water, and combinations thereof. In certain embodiments, the chemical composition includes air. In certain embodiments, the chemical composition is a sample of its native form. In certain embodiments, the chemical composition includes a solvent. Such a solvent can include various solvents from the environment, or an industrial or laboratory solvent. In certain embodiments, the solvent includes a single solvent or more than one solvent. In certain embodiments, the solvent includes a liquid, a gas, a sold, or a combination thereof. In certain embodiments, the solvent includes an organic solvent, an inorganic solvent, or combination thereof. In certain embodiments, the solvent includes one or more of water, alcohols, dioxane, toluene, dimethyl formamide, hexanes, chloroform, acetonitrile, pyridine, deuterium oxide, and combinations thereof. In certain embodiments, the solvent includes one or more of D2O, dimethylsulfoxide, methanol, ethanol, acetone, n-propanol, butanone, dichloromethane, diethyl ether, benzene, hexane, and combinations thereof. In certain embodiments, the chemical composition includes one or more solutes. Such a solute can include, without limitation, sodium fluoride, sodium chloride, sodium bromide, sodium iodide, and combinations thereof. In certain embodiments, the one or more solvents includes a trace chemical or a trace contaminant in the chemical composition. Such embodiments can provide a benefit of the high-capacity analysis of multi-phase fluids, organics, liquids, vapors, and gases.

In more detail, in embodiments, the probes can detect trace H2O in D2O; trace methanol in methanol-d4; trace ethanol in ethanol-d6; water in acetaldehyde; water in acetonitrile; water in 1,2-butanediol; water in 1,3-butanediol; water in 1,4-butanediol; water in 2-butoxyethanol; water in diethanolamine (DEA); water in diethylene glycol; water in diethylene glycol dimethyl ether; water in diethylene triamine (DETA); water in 1,2-dimethoxyethane (DME); water in dimethylformamide (DMF); water in dimethylsulfoxide (DMSO); water in 1,4-dioxane; water in ethanol; water in ethylamine; water in ethylene glycol; water in furfuryl alcohol; water in glycerin; water in hexamethylphosphoramide (HMPA); water in hexamethylphosphorous triamide (HMPT); water in methanol; water in methyl isocyanide; water in n-methyl-2-pyrrolidone; water in 1-propanol; water in 2-propanol; water in 1,3-propanediol; water in 1,5-propanediol; water in pyridine; water in tetrahydrofuran (THF); water in triethylene glycol; trace fluoride in water; trace cyanide in water; H2O in ultra-high purity gas streams (including N2, Ar, CH4, H2); NH3 in gas streams (e.g. CH4, H2); H2S contaminants in gas streams; H2Se contaminants in gas streams; acetone purity; acidity (as acetic acid) in acrylonitrile; aldehydes in styrene; alkyl nitrate in diesel fuels; ammonia/amines in LPG; aromatics in methanol by UV; ethanol purity by GC; ethyl benzene purity; ethyl mercaptan in LP; fluoride; hexene-1 purity; hydrogen sulfide and arsine in gaseous fuels; hydrogen sulfide and mercaptan sulfur in liquid hydrocarbon; hydrogen sulfide and sulfur dioxide in aromatic hydrocarbons; hydrogen sulfide in fuel oil; hydrogen sulfide in vapor phase; hydrogen sulfide, mercaptan sulfur, and carbonyl sulfide in hydrogen gases; low concentrations of diethylene glycol in ethylene glycol; methanol purity; methyl ethyl ketone (MEK) purity; methyl isobutyl ketone purity; moisture content; phenol content of cumene; thiophene in benzene; water content in most liquids no otherwise recited; trace water in methanol-d4; water in DMSO-d6; trace water in ethanol-d6; acetaldehyde content in vinyl acetate; acetone content in methanol; acidity in ethanol; acidity in glycols; acidity in vinyl acetate and acetaldehyde; acidity in volatile solvents; alkalinity in acetone; alkalinity in LPG; amyl nitrate in diesel fuels; aromatics in aviation fuel by HPLC; aromatics in gasoline by GC/GCMS; aromatics in hydrocarbons by GC; aromatics in n-paraffin by UV; benzene and DCPD in organic solvents; carbonyls content in liquids; dryness in propane; fatty acid methyl esters (FAME) in ethanol; fatty acid methyl esters in aviation turbine fuel; fluorinated organics in water; free halogens in halogenated organic solvents; glycol impurities in mono, di, tri, and tetraethylene glycol; glyphosate in water; methanol in crude oil by GC; methanol in crude oil by water extraction; organic acids (as phenolic compounds) in heavy hydrocarbons; peroxides in various solvents; sulfates in ethanol; and/or trace amounts of peroxide in organic solvents.

In an embodiment, it is believed that the probes can allow for the following analytes to be identified, traced, and/or quantified: acetic acid; acetone; ammonia; butyl acetate; carbon tetrachloride; chlorobenzene; ethanol; ethyl lactate; ethylene glycol monomethyl ether; formaldehyde; hydrogen chloride; hydrogen selenide; hydrogen sulfide; isopropanol; methanol; methyl ethyl ketone; methyl isobutyl ketone; nitrous oxide; phenol; propanol; propylene glycol; trichlorobenzene; trichloroethylene; trichloroethane; toluene; xylene; arsenic penafluoride; arsine; boron trichloride; boron trifluoride; chlorine trifluoride; chromic phosphoric acid; diborane; dichlorosilane; dimethylbenzene; dimethylzinc; disilane; ethylbenzene; germane; hexamthyldisilazane; hydrofluoric acid; n-methyl pyrrolidone; nitrogen trifluoride; phosgene; phosphine; phosphoric acid; phosphorus pentafluoride; silicon tetrachloride; silicon tetrafluoride; sulfur hexafluoride; tellurium hexafluoride; trimethyl aluminum; trimethyl gallium; trimethyl indium; tungsten hexafluoride; ammonium hydroxide; hydrochloric acid; potassium hydroxide; propylene glycol monomethyl ether acetate; sodium hydroxide; and/or sulfuric acid Embodiments of methods herein include contacting the probe with the chemical composition for a test duration. Such a test duration in various embodiments can range from about 1 second to 5 minutes. Generally, if a test is carried out too quickly, then the material may not be saturated with analyte, resulting in an erroneous reading. For example, in some purity tests, if a reading was taken too quickly, it would give a higher purity reading due to the fact the material has not had time to properly react with the analyte.

In certain embodiments, one or more chemical compositions can be contacted with the probe for one or more test durations. In certain embodiments, methods herein allow immediate solvent identification by color changes visible to the naked eye upon contact of the probe with a chemical composition. In certain embodiments, the method includes pre-scanning the array of luminescent chemical sensors prior to contacting the probe with the chemical composition for the test duration. Such embodiments can provide a benefit of providing a "baseline" reading of the chemical sensors before they are reacted with a chemical composition, thus helping to ensure there is no contamination of the probe and that the chemical sensors have the necessary viability before performing a chemical analysis and inconsistencies in luminescence between batches.

Embodiments of methods herein include exposing the probe to a test range of light; in an embodiment, the test range of light includes light in a range of from about 280 nm to about 400 nm. In certain embodiments, the test range of light includes light in a range of from about 300 nm to about 380 nm. In certain embodiments, the test range of light includes light in a range of from about 320 nm to about 350 nm. In such embodiments, interaction between the luminescent chemical sensors and one or more chemicals in the chemical composition results in emission of a specific signature color and intensity of visible light by the luminescent chemical sensors, upon exposing the probe to a test range of light. In certain embodiments, a particular chemical in a chemical composition produces a unique eight-factor signature of color and brightness; this light signature can be used to identify and quantify the chemicals present in the chemical composition.

Embodiments of the present disclosure can present an advantage of a configuration that allows the probes to display a multi-factor signature of color and brightness in response to the presence of a wide variety of chemicals present in chemical compositions. In various embodiments, an array of luminescent chemical sensors includes different lanthanide containing phosphorous compounds in varied ionic ratios configured to provide discernable responses in color and intensity of emitted light in response to the presence of a very different variety of chemical compounds. For example, such compounds can include solvents that differ from each other as much as methanol, water, and toluene, yet all such solvents can potentially be identified both qualitatively and quantitatively in a single assay. Such compounds can also include chemicals that are very similar to each other, for example, water and deuterium, yet compounds such as these can also be distinguished by the chemical analysis methods herein, even in trace amounts. Where one ionic weight ratio might provide a certain degree of specificity and sensitivity for chemical analysis, the addition of more weight ratios of lanthanide ions in the phosphorous compounds of the chemical sensors can add to the sensitivity and specificity of the analysis, still in a compact single assay format. In an embodiment, the array of luminescent chemical sensors includes at least four different weight ratio combinations of three different lanthanide ions included in the lanthanide containing phosphorous compounds. Each of the four weight ratio combinations among the array of chemical sensors provides a unique color signal and intensity signal in response to the presence of each chemical and chemical concentration, thus providing a unique eight-factor "fingerprint" for each chemical and chemical concentration, all readable in a single compact assay format.

In certain embodiments, the luminescent compounds can be purified before exposure to a chemical composition. In certain embodiments, the luminescent compound is heated prior to exposure to a chemical composition. In certain embodiments, the luminescent compound is dried prior to exposure to a chemical compound. Drying may include air drying, drying using a heat gun, drying using a vacuum, or other suitable drying method. In certain embodiments, purifying the luminescent compounds before exposure to a chemical composition reduces or eliminates the amount of solvents or impurities associated with synthesis of the luminescent compounds. Such embodiments can provide a benefit of increasing the accuracy and sensitivity of chemical analyses using the probes.

In certain embodiments, provided there is at least one chemical substance in the chemical composition, the method includes identifying the at least one chemical substance in the chemical composition based on a measurement of the color and the intensity of luminescence of the array of luminescent chemical sensors. In certain embodiments, the method includes measuring a concentration of a chemical substance in the chemical composition based on a measurement of the color and the intensity of luminescence of the array of luminescent chemical sensors. Such embodiments can provide a benefit of not only detecting but measuring chemical targets. In other embodiments, such methods can allow quantitative chemical analysis by simple spectrophotometry, compatible with a broad range of solvents yielding results in minutes, not days. In certain embodiments, the chemical composition is in a liquid or a vapor phase. In certain embodiments, the at least one chemical substance includes deuterium, and the chemical composition includes water. Such embodiments can provide a benefit of detection of low levels of water in solvents, allowing for a variety of quality assurance testing.

In certain embodiments, the method includes measuring the concentration of the at least one chemical substance in the chemical composition by comparing a ratio of wavelengths of luminescence emitted by a test sample to wavelengths of luminescence emitted by a concentration standard. In certain embodiments, the wavelengths of luminescence emitted by a concentration standard are in the range of visible light. In certain embodiments, the ratio is a ratio of visible wavelengths of light. In certain embodiments, the ratio of wavelengths of luminescence emitted by a test sample includes a ratio of 543 nm/616 nm. In certain embodiments, the ratio of wavelengths of luminescence emitted by a test sample includes a ratio of 543 nm/616 nm/510 nm.

In certain embodiments, provided the probe further includes an identification tag mounted on the base layer, the method includes identifying the probe by scanning the identification tag.

Methods of Manufacturing a Probe of Various Embodiments

The present disclosure relates to methods of manufacturing a probe for analyzing a chemical composition. Various embodiments of such methods herein include mounting an array of luminescent chemical sensors on an upper surface of a platform. In such embodiments, the array of luminescent chemical sensors can include at least one detection sensor, at least one control sensor, or a combination thereof. In various embodiments, the at least one detection sensor, if present, includes a combination of two or more detection lanthanide containing phosphorous compounds mounted onto a detection area of the platform. In various embodiments, the at least one control sensor, if present, includes at least one control lanthanide containing phosphorous compound mounted onto a control area of the platform.

In certain embodiments, mounting the array of luminescent chemical sensors on the upper surface of the platform includes spray coating the at least one detection sensor, the at least one control sensor, or a combination thereof, onto the platform. In such embodiments, the at least one control and/or at least one detection sensors can be directly and selectively spray coated onto a control area and/or a detection area of the platform, respectively. Such embodiments can provide a benefit of rapid manufacturing of probes having the desired composition of luminescent chemical sensors in the arrays. Such embodiments can provide a benefit of probes having a small thickness, due to the array of luminescent chemical sensors being directly applied to the platform material. In certain embodiments, the probes can have a thickness of from about 1 mm to about 2 mm.

In certain embodiments, the method further includes heating the platform during or after spray coating. In certain embodiments, the heating can be performed at a temperature of from about 80 degrees Celsius to about 120 degrees Celsius. In certain embodiments, the heating can be performed at a temperature of from about 90 degrees Celsius to about 110 degrees Celsius. In certain embodiments, the heating can be performed at a temperature of from about 95 degrees Celsius to about 100 degrees Celsius. In certain embodiments, the heating can be performed for a time period of from about 1 hour to about 10 hours. In certain embodiments, the heating can be performed for a time period of from about 2 hours to about 8 hours. In certain embodiments, the heating can be performed for a time period of from about 3 hours to about 6 hours.

In certain embodiments, the platform is formed from a single piece of a fibrous material. In some embodiments, the platform can be formed from more than one fibrous material. In certain embodiments, the platform is formed from a binder free fibrous material. In certain embodiments, the platform is formed from a binder free borosilicate microfiber material, a binder free glass microfiber material, a binder free quartz microfiber material, a cotton material, or a combination thereof.

Various embodiments of a method of manufacturing a probe herein include mounting at least two lining strips to the top and bottom of an upper surface of the platform, and adhering a lower surface of the platform to a base layer to form a probe. Such embodiments are applicable when adhering the lower surface of the platform to the base layer includes ultrasonic welding. In certain embodiments, the at least two lining strips are aligned at the top and bottom of the platform upper surface and in contact with a portion of the platform material; in such embodiments, ultrasonic welding results in adhering the lower surface of the platform to the base layer. Such embodiments can provide a benefit of adhering or fastening the platform to the base layer without the use of a binder.

In certain embodiments, the at least two lining strips are formed from a plastic material. Such a plastic material can include any plastic material suitable for an ultrasonic welding process, including but not limited to a polyester material, a PET (polyethylene terephthalate) material, a polystyrene material, a polyvinyl chloride material, and combinations thereof.

In certain embodiments, the base layer is formed from a plastic material. Such a plastic material can include any plastic material suitable for an ultrasonic welding process, including but not limited to a polyester material, a PET material, a polystyrene material, a polyvinyl chloride material, and combinations thereof.

In certain embodiments, the method further includes cutting the platform, base layer and at least two lining strips to form a plurality of probes. Such embodiments can provide for the rapid manufacturing of a number of probes having desired dimensions, from a single manufactured larger probe.

Additional Embodiments

Embodiment 1. A probe for analyzing a chemical composition comprising: an array of luminescent chemical sensors mounted on a base layer, wherein the array of luminescent chemical sensors includes at least one control sensor and at least one detection sensor, wherein the at least one control sensor includes at least one control lanthanide containing phosphorous compound mounted onto a control area of a control platform and the at least one detection sensor includes a combination of two or more detection lanthanide containing phosphorous compounds mounted onto a detection area of a detection platform, wherein the control platform and the detection platform are adhered to the base layer.

Embodiment 2. The probe of embodiment 1, wherein the array of luminescent chemical sensors includes from 1 to 3 control sensors and from 1 to 50 detection sensors; or the array of luminescent chemical sensors includes 2 control sensors and from 1 to 50 detection sensors.

Embodiment 3. The probe of any of embodiments 1-2, wherein the control platform and the detection platform include a fibrous material, and the control platform and the detection platform are mounted on separate fibrous materials.

Embodiment 4. The probe of any of embodiments 1-3, wherein the fibrous material includes a cellulosic material, a paper material, a silicone paper material, or a combination thereof.

Embodiment 5. The probe of any of embodiments 1-4, wherein the at least one control lanthanide containing phosphorous compound is mounted directly onto the control platform without a binder; or wherein the detection lanthanide containing phosphorous compounds are mounted directly onto the detection platform without a binder.

Embodiment 6. The probe of any of embodiments 1-5, wherein at least one of the control platform and the detection platform has a thickness of from about 0.1 mm to about 2 mm; or wherein at least one of the control platform and the detection platform has a thickness of about 1 mm or less; or wherein at least one of the control platform and the detection platform has a longest measurement of from about 2 mm to about 60 mm; or wherein at least one of the control area and the detection area have a square shape, a rectangular shape, a circular shape, an ovular shape, a triangular shape, a hexagonal shape, a polygonal shape, or a combination thereof.

Embodiment 7. The probe of any of embodiments 1-6, wherein the at least one control lanthanide containing phosphorous compound includes at least one rare earth ion selected from the group consisting of La, Ce, Pr, Nd, Pm, Sm, Eu, Gd, Tb, Dy, Ho, Er, Tm, Yb, Lu, and Y.

Embodiment 8. The probe of any of embodiment 1-7, wherein the combination of two or more detection lanthanide containing phosphorous compounds includes at least 2 different rare earth ions, wherein the rare earth ions are selected from the group consisting of La, Ce, Pr, Nd, Pm, Sm, Eu, Gd, Tb, Dy, Ho, Er, Tm, Yb, Lu, and Y.

Embodiment 9. The probe of any of embodiments 1-8, wherein the array of luminescent chemical sensors includes a lower wavelength control sensor and a higher wavelength control sensor, wherein the lower wavelength control sensor contains a lower wavelength ion X, wherein the higher wavelength control sensor contains a higher wavelength ion Z, wherein X and Z are different; wherein the array of luminescent chemical sensors includes at least one detection sensor containing a weight ratio of the lower wavelength ion X to the higher wavelength ion Z, wherein the weight ratio ranges from about 10:1 X:Z to about 1:10 X:Z.

Embodiment 10. The probe of any of embodiments 1-9, wherein the at least one detection sensor includes at least 2 lanthanide ions selected from the group consisting of Eu, Gd, and Tb; and wherein a weight ratio of the at least 2 lanthanide ions includes about 5:1 Tb:Eu, about 1:5 Tb:Eu, about 1:1:1 Eu:Gd:Tb, about 3:1:1 Eu:Gd:Tb, about 1:1:3 Eu:Gd:Tb, or about 1:3:1 Eu:Gd:Tb.

Embodiment 11. The probe of any of embodiments 1-10, wherein the base layer is formed of plastic, a paper, or wood, and the base layer has a length and a width equal to or greater than the array of luminescent chemical sensors; or the base layer forms a handle portion, which is located from about 1 mm to about 10 mm from the array of luminescent chemical sensors.

Embodiment 12. The probe of embodiments 1-11, wherein the probe further includes an identification tag mounted on the base layer.

Embodiments 13. The probe of any of embodiments 1-12, wherein the identification tag includes an optical tag or a radio frequency tag; or wherein the identification tag is mounted on a bottom of the probe or on a handle of the probe.

Embodiment 14. A method of analyzing a chemical composition comprising: providing a probe, wherein the probe includes an array of luminescent chemical sensors mounted on a base layer, wherein the array of luminescent chemical sensors includes at least one control sensor and at least one detection sensor, wherein the at least one control sensor includes at least one control lanthanide containing phosphorous compound mounted onto a control area of a control platform and the at least one detection sensor includes a combination of two or more detection lanthanide containing phosphorous compounds mounted onto a detection area of a detection platform, wherein the control platform and the detection platform are adhered to the base layer; contacting the probe with the chemical composition for a test duration; exposing the probe to a test range of light; and measuring a color and an intensity of luminescence of the array of luminescent chemical sensors.

Embodiment 15. The method of embodiment 14, provided there is at least one chemical substance in the chemical composition, further comprising identifying the at least one chemical substance in the chemical composition based on a measurement of the color and the intensity of luminescence of the array of luminescent chemical sensors; or measuring a concentration of a chemical substance in the chemical composition based on a measurement of the color and the intensity of luminescence of the array of luminescent chemical sensors.

Embodiment 16. The method of any of embodiments 14-15, wherein the chemical composition is in a liquid or a vapor phase.

Embodiment 17. The method of any of embodiments 14-16, further comprising, pre-scanning the array of luminescent chemical sensors prior to contacting the probe with the chemical composition for the test duration.

Embodiment 18. The method of any of embodiments 15-17, wherein the at least one chemical substance includes deuterium, and the chemical composition includes water.

Embodiment 19. The method of any of embodiments 15-18, further comprising, measuring the concentration of the at least one chemical substance in the chemical composition by comparing a ratio of wavelengths of luminescence emitted by a test sample to wavelengths of luminescence emitted by a concentration standard.

Embodiment 20. The method of any of embodiments 14-19, further comprising, provided the probe further includes an identification tag mounted on the base layer; identifying the probe by scanning the identification tag.

EXAMPLES

Example 1: Synthesis of Ln-PCM-22

All Ln-PCM-22 materials were synthesized by the same method with appropriate proportions of lanthanide(III) nitrate hydrate precursors: tris(p-carboxylato) triphenylphosphine, $P(C6H4-4-CO2H)3$ (0.5 to 0.3 mmol) was dissolved in a DMF/dioxane/H2O mixture (2.0 to 5.0 cm3). A second solution of the requisite $Ln(NO3)3 \times H2O$ salt(s) (0.1 to 0.4 mmol total) was prepared in the same solvent mixture (2.0 to 5.0 cm3). The two solutions were then combined and agitated briefly before being heated at 70-85° C. for 3-4 days. Crystalline products were recovered by decantation and washing with fresh solvent before being air dried.

Example 2: Preparation of Probe Assemblies

To demonstrate the potential applicability of the sensor materials in conventional paper-based disposable sensors, model dip-stick assemblies were prepared by depositing small amounts of the as-synthesized sensor materials onto glass slides by using spray glue to adhere the crystallites. The materials were desolvated in air with a heat gun and then immersed in different solvents, which induced immediate color changes that were seen when viewed under a 354 nm lamp.

Example 3: Trace H2O Detection in D2O and Other Solvents by Eu:Tb-PCM-22

All dry crystalline materials were activated in small Schlenk flasks by heating under vacuum for 18 hours in a silicone oil bath. Aliquots (1-5 mg) of the desolvated materials were used for each spectrophotometric measurement. Trace H2O solvent mixtures were prepared by a series of serial dilutions from a known stock solution until the desired ppm concentrations were obtained.

The limits of detection were then assessed for trace H2O in acetone, acetonitrile, ethanol, and D2O. The mixed Eu:Tb-PCM-22 could quantify H2O down to 0.1% v/v in these organic solvents; it also provided a visual response to H2O between 0.5% and 5%. This sensor material also had the remarkable ability to detect H2O in D2O in the range of 10-100 ppm. The sensor response for H2O in D2O was essentially linear over the entire range of 10-120,000 ppm.

Example 4: Ternary Eu:Gd:Tb-PCM-22 Materials for Eight-Factor Solvent Fingerprinting To improve the sensitivity of PCM-22 toward a much broader range of analytes, a series of three-metal sensor materials (EuX:GdY:TbZ) were synthesized.

The Eu:Gd:Tb-PCM-22 materials were desolvated and exposed to 18 common solvents with diverse chemical functionalities and polarities (with dielectric constants, $\varepsilon r=1.89-79.8$). The resulting emission spectra were recorded for the generation of a unique eight-factor fingerprint profile for each solvent. The eight factors are derived from the emission color intensity emission (CIE) coordinates for the four Eu:Gd:Tb compositions and the relative emission intensities of each (Irelative={(I543 nm/I616 nm)/I510 nm}). For the 18 solvents tested, the eight-factor fingerprints obtained were spectroscopically unique: Eu:Gd:Tb-PCM-22 acts as a sensor for very rapid solvent identification, which is internally calibrated by the monitoring of relative intensities at three wavelengths with only one excitation wavelength.

A reference chart was derived for comparison of the eight-factor fingerprints for each solvent. Each unique fingerprint is shown as four CIE colored spheres in which the visible size of each sphere is directly proportional to the magnitude of its brightness (Irelative). Solvents in the chart are organized by decreasing dielectric constant (polarity). Even for chemically similar solvents, the eight-factor fingerprint is definitive. For example, the C1-C3 n-alcohols are differentiated by a decrease in brightness with increasing alkyl chain length, as well as a shift toward redder emission. Common ketones (acetone and butanone) and aromatics (benzene, pyridine, and toluene) are distinctly identifiable. Selectivity is not limited to changes in molecular volume; the halogenated solvents CH2Cl2 and CH3Cl also show distinct differences as a result of the different quenching abilities of C—H versus C—Cl bonds.

Example 5: Manufacturing of Probes Using Spray Coating and Ultrasonic Welding

Probes were constructed according to the following protocol:

1. An array of PCM-22 luminescent chemical sensors was spray coated onto binder free platform materials (Ahlstrom-Munksjö, product numbers Grades 121, Grade 141, Grade 151, Grade 222, Grade 237, Grade 238, Grade 270, Grade 319, Grade 320; Cytiva Standard 14, 1882-866, 1851-865, I.W. Tremont B-85, Grade C, Grade D-23, Grade F). Heating was applied during or after spray coating at 100 degrees Celsius for 2 hours.

2. Each platform was aligned over a plastic backing base layer, and two plastic lining strips were aligned on the top and bottom of the platform upper surface.

3. Ultrasonic welding was applied to adhere the lower surface of each platform to the plastic backing base layer.

4. The probes were cut into multiple probes having the desired diameter.

What is claimed is:

1. A probe for analyzing a chemical composition comprising:
    an array of luminescent chemical sensors mounted on platforms, wherein the platforms include a detection platform and a control platform,
    wherein the array of luminescent chemical sensors includes at least one detection sensor, at least one control sensor, or a combination thereof,
    wherein the at least one detection sensor includes a combination of two or more detection lanthanide containing phosphorous compounds mounted onto a detection area of the detection platform;
    wherein the at least one control sensor includes at least one control lanthanide containing phosphorous compound mounted onto a control area of the control platform; and
    wherein the control platform and the detection platform are adhered to a base layer,
    wherein the at least one control lanthanide containing phosphorous compound is mounted directly onto the control platform without a binder; or
    wherein the combination of two or more detection lanthanide containing phosphorous compounds are mounted directly onto the detection platform without a binder.

2. The probe of claim 1, wherein the array of luminescent chemical sensors includes from 1 to 3 control sensors and from 1 to 50 detection sensors; or
    the array of luminescent chemical sensors includes 2 control sensors and from 1 to 50 detection sensors.

3. The probe of claim 1, wherein at least one of the control platform and the detection platform has a thickness of from about 0.1 mm to about 2 mm; or
    wherein at least one of the control platform and the detection platform has a longest measurement of from about 2 mm to about 60 mm; or
    wherein at least one of the control area and the detection area have a square shape, a rectangular shape, a circular shape, an ovular shape, a triangular shape, a hexagonal shape, a polygonal shape, or a combination thereof.

4. The probe of claim 1, wherein the at least one control lanthanide containing phosphorous compound includes at least one rare earth ion selected from the group consisting of $La^{3+}$, $Ce^{3+}$, $Pr^{3+}$, $Nd^{3+}$, $Pm^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, and $Y^{3+}$.

5. The probe of claim 1, wherein the combination of two or more detection lanthanide containing phosphorous compounds includes at least 2 different rare earth ions, wherein the rare earth ions are selected from the group consisting of $La^{3+}$, $Ce^{3+}$, $Pr^{3+}$, $Nd^{3+}$, $Pm^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, $Lu^{3+}$, and $Y^{3+}$.

6. The probe of claim 1, wherein the array of luminescent chemical sensors includes a lower wavelength control sensor and a higher wavelength control sensor adhered to the base layer, wherein the lower wavelength control sensor contains a lower wavelength ion X, wherein the higher wavelength control sensor contains a higher wavelength ion Z, wherein X and Z are different;
    wherein the array of luminescent chemical sensors includes the at least one detection sensor containing a weight ratio of the lower wavelength ion X to the higher wavelength ion Z, wherein a range of the weight ratio has a range of from about 10:1 X:Z to about 1:10 X:Z.

7. The probe of claim 1, wherein the at least one detection sensor includes at least 2 lanthanide ions selected from the group consisting of $Eu^{3+}$, $Gd^{3+}$, and $Tb^{3+}$; and wherein a weight ratio of the at least 2 lanthanide ions includes about 5:1 $Tb^{3+}$:$Eu^{3+}$, about 1:5 $Tb^{3+}$:$Eu^{3+}$, about 1:1:1 $Eu^{3+}$:$Gd^{3+}$:$Tb^{3+}$, about 3:1:1 $Eu^{3+}$:$Gd^{3+}$:$Tb^{3+}$, about 1:1:3 $Eu^{3+}$:$Gd^{3+}$:$Tb^{3+}$, or about 1:3:1 $Eu^{3+}$:$Gd^{3+}$:$Tb^{3+}$.

8. The probe of claim 1, wherein the base layer is formed of plastic, a paper, or wood, and the base layer has a length and a width equal to or greater than the array of luminescent chemical sensors; or
    the base layer forms a handle portion, which is located from about 1 mm to about 10 mm from the array of luminescent chemical sensors.

9. The probe of claim 1, wherein the probe further includes an identification tag mounted on the base layer.

10. The probe of claim 9, wherein the identification tag includes an optical tag or a radio frequency tag; or wherein the identification tag is mounted on a bottom of the probe or on a handle of the probe.

11. A probe for analyzing a chemical composition comprising:
    an array of luminescent chemical sensors comprising at least one detection sensor and at least one control sensor,
    wherein the at least one detection sensor includes a detection area on at least one detection platform and the at least one control sensor includes a control area on at least one control platform;
    wherein the at least one detection sensor includes a combination of two or more detection lanthanide containing phosphorous compounds mounted onto the detection area of the at least one detection platform;
    wherein the at least one control sensor includes at least one control lanthanide containing phosphorous compound mounted onto the control area of the at least one control platform;
    wherein the at least one control platform and the at least one detection platform include a fibrous material, and the at least one control platform and the at least one detection platform are made of separate fibrous materials; and
    wherein the at least one control platform and the at least one detection platform adhere to a base layer.

12. The probe of claim 11, wherein the fibrous material includes a cellulosic material, a paper material, a silicone paper material, a borosilicate microfiber material, a glass microfiber material, a quartz microfiber material, a cotton fiber, or a combination thereof.

* * * * *